US012583830B2

(12) United States Patent
Qian

(10) Patent No.: US 12,583,830 B2
(45) Date of Patent: Mar. 24, 2026

(54) SYNTHESIS METHOD FOR SYNTHESIZING OXETANE DERIVATIVE BY MICROREACTOR

(71) Applicants: Changzhou Tronly New Electronic Materials Co., Ltd., Jiangsu (CN); Changzhou Tronly Advanced Electronic Materials Co., Ltd., Jiangsu (CN)

(72) Inventor: Xiaochun Qian, Jiangsu (CN)

(73) Assignees: Changzhou Tronly Advanced Electronic Materials Co., Ltd., Changzhou (CN); Changzhou Tronly Advanced Electronic Materials Co., Ltd., Changzhou (CN)

( * ) Notice: Subject to any disclaimer, the term of this patent is extended or adjusted under 35 U.S.C. 154(b) by 854 days.

(21) Appl. No.: 17/913,671

(22) PCT Filed: Mar. 16, 2021

(86) PCT No.: PCT/CN2021/081185

§ 371 (c)(1),
(2) Date: Sep. 22, 2022

(87) PCT Pub. No.: WO2021/197057

PCT Pub. Date: Oct. 7, 2021

(65) Prior Publication Data

US 2023/0116611 A1 Apr. 13, 2023

(30) Foreign Application Priority Data

Apr. 3, 2020 (CN) ......................... 202010261424.9
Feb. 10, 2021 (CN) ......................... 202110184195.X

(51) Int. Cl.
*C07D 305/06* (2006.01)

(52) U.S. Cl.
CPC .................................. *C07D 305/06* (2013.01)

(58) Field of Classification Search
CPC .................................................... C07D 305/06
See application file for complete search history.

(56) References Cited

U.S. PATENT DOCUMENTS

| | | | |
|---|---|---|---|
| 5,463,084 | A | 10/1995 | Crivello et al. |
| 5,750,590 | A | 5/1998 | Schaefer et al. |
| 2011/0236269 | A1 | 9/2011 | Inoue et al. |

FOREIGN PATENT DOCUMENTS

| | | |
|---|---|---|
| CN | 104876807 | 9/2015 |
| CN | 104892549 | 9/2015 |
| CN | 110845643 | 2/2020 |
| JP | 1994016804 | 1/1994 |
| JP | 2000086646 | 3/2000 |
| JP | 2002138084 | 5/2002 |
| JP | 2007217471 | 8/2007 |
| JP | 2011200004 | 2/2011 |
| JP | 2017133039 | 8/2017 |
| WO | WO 2004/106314 | 12/2004 |
| WO | WO 2010032712 | 3/2010 |

OTHER PUBLICATIONS

Translation of International Search Report for corresponding PCT Appl No. PCT/CN2021/081185, dated Jun. 22, 2021.
Crivello, "'Kick-Starting' Oxetane Photopolymerizations," J. Polym. Sci., Part A: Polym. Chem., Aug. 2014, 52:2934-2946.
Extended European Search Report in European Appln No. 21780711.4, dated Mar. 13, 2024, 9 pages.
Office Action in Chinese Appln. No. 202110184195.X, dated Feb. 28, 2024, 13 pages (with English translation).
Office Action in Japanese Appln. No. 2022-560041, dated Jan. 30, 2024, 8 pages (with English translation).
Roberge et al., "Microreactor Technology: A Revolution for the Fine Chemical and Pharmaceutical Industries?" Chemical Engineering & Technology, Mar. 2005, 28(3):318-323.
Yao et al., "Review of the applications of microreactors," Renewable and Sustainable Energy Reviews, Jul. 2015, 47(2015):519-539.
Yoshida et al., "Selective Organic Reactions Using Microreactors," Journal of Synthetic Organic Chemistry, May 2005, 63(5):93-104 (with English abstract only).
Office Action in JP Appln. No. 2022-560041, dated Aug. 9, 2023, 10 pages (with English translation).

*Primary Examiner* — Golam M Shameem
(74) *Attorney, Agent, or Firm* — Fish & Richardson P.C.

(57) ABSTRACT

The invention provides a synthesis method for synthesizing an oxetane derivative by a microreactor. The synthesis method comprises: delivering 3-ethyl-3-hydroxymethyloxetane, a raw material Ha, a catalyst, and an alkali into a microreactor, and performing an etherification reaction so as to obtain an etherification product system, the raw material Ha having a general formula of $R-(X)_n$, and X being a halogen; and separating the etherification product system so as to obtain the oxetane derivative. The microreactor is used for greatly improving the mass and heat transfer properties of the reaction system, reducing the reaction time, improving the production efficiency, increasing the yield of the product, achieving the continuity and automation of the process, and improving the safety of the process. In addition, the reaction device required by the described synthesis process requires has a small size, requires less manpower and has high safety.

11 Claims, 1 Drawing Sheet

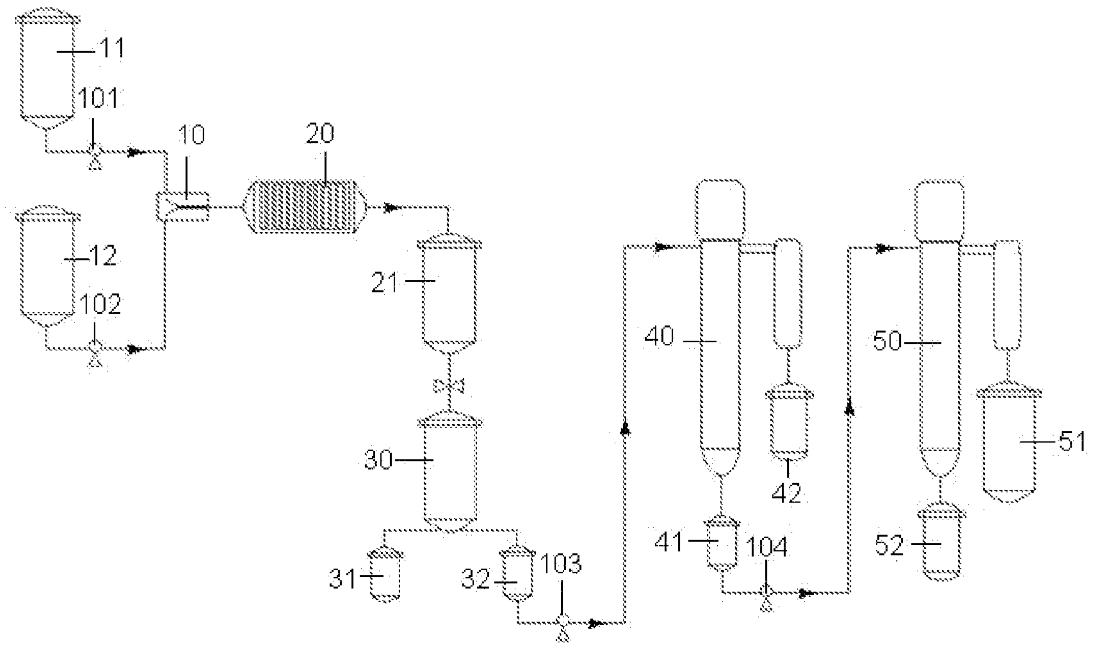
11
101
10
20
12
102
21
30
31
32
103
40
41
42
104
50
51
52

SYNTHESIS METHOD FOR SYNTHESIZING OXETANE DERIVATIVE BY MICROREACTOR

CROSS-REFERENCE TO RELATED APPLICATIONS

This application is a U.S. National Phase application under 35 U.S.C. § 371 of International Patent Application No. PCT/CN2021/081185, filed on Mar. 16, 2021, which claims priority to Chinese Application No. 202110184195.X, filed on Feb. 10, 2021 and Chinese Application No. 202010261424.9, filed on Apr. 3, 2020. The entire contents of the parent applications are hereby incorporated by reference.

TECHNICAL FIELD

The invention relates to the field of organic synthesis, in particular to a synthesis method for synthesizing an oxetane derivative by a microreactor.

BACKGROUND

Using 3-ethyl-3-hydroxymethyloxetane as raw material, the etherification reaction with a halogenated organic compound under the action of a base can obtain a series of oxetane derivatives, which can be used as monomers in a photocurable cation system, and applied in the fields of photocurable inks, coatings, adhesives, and the like. The representative products are 3-ethyl-3-[(oxiranyl-2-methoxy) methyl]oxetane, bis [1-ethyl(3-oxetanyl)methyl]ether, and 3-benzyloxymethyl-3-ethyloxetane. These oxetane products have become one of the raw materials having the most promising market potentials in the field of cationic photocuring due to their low viscosity, good dilutability, fast crosslinking rate, and excellent performances after film-forming.

Taking 3-ethyl-3-[(oxiranyl-2-methoxy)methyl]oxetane as an example, its industrial production is to use 3-ethyl-3-hydroxymethyloxetane and epichlorohydrin as raw materials for etherification reaction under the action of solid sodium hydroxide. Since the reaction system is a liquid-solid heterogeneous phase and the mass transfer is relatively difficult, epichlorohydrin and sodium hydroxide should be excess by more than 50% in order to ensure the conversion rate. The production is conducted in a 2 $m^3$ reaction kettle, and the reaction process takes about 12 h. The post-treatments including filtration, rectification, and other processes take about 30 h. The operation that solid sodium hydroxide is added in batches during the reaction is cumbersome and has safety hazards such as temperature runaway.

In view of the existence of the above problems, it is necessary to provide a method for synthesizing an oxetane derivative with short reaction time, high mass transfer efficiency, and good safety.

SUMMARY

A main object of the invention is to provide a synthesis method for synthesizing an oxetane derivative by a microreactor, so as to solve the problems present in the existing synthesis methods for oxetane derivatives such as long reaction time, cumbersome operations, and poor safety. The selectivity of etherification reaction is ensured while realizing the continuous production, and the product yield is improved.

In order to achieve the above object, the invention provides a synthesis method for synthesizing an oxetane derivative by a microreactor, the oxetane derivative having the structure shown in Formula (I):

Formula (I)

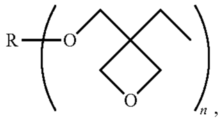

wherein R is a $C_2$ to $C_{12}$ linear or branched alkyl, an alkyl containing ethylene oxide structure, an alkyl containing oxetane structure, phenyl, tolyl, benzyl, or biphenyl, and n is 1-4; the synthesis method for synthesizing an oxetane derivative by a microreactor as above including: feeding 3-ethyl-3-hydroxymethyloxetane, a raw material Ha, a catalyst, and a base into a microreactor for etherification reaction to obtain an etherification product system, wherein the raw material Ha has a general formula of $R-(X)_n$, and X is halogen; and subjecting the etherification product system to separation to obtain the oxetane derivative.

Further, the microreactor has a reaction channel having an inner diameter of 200 to 10,000 μm.

Further, the base is an alkali metal compound or an aqueous solution of alkali metal compound, and the alkali metal compound is selected from one or more of the group consisting of lithium hydroxide, sodium hydroxide, potassium hydroxide, and calcium hydroxide; preferably, the alkali metal compound is sodium hydroxide; the concentration of the aqueous solution of alkali metal compound is 10% to 20%; the catalyst is selected from one or more of the group consisting of polyethers, cyclic polyethers, and quaternary ammonium salts.

Further, the catalyst is selected from one or more of the group consisting of polyethylene glycol, polyethylene glycol alkyl ether, 18-crown-6, 15-crown-5, tetraethylammonium bromide, tetrabutylammonium bromide, tetrabutylammonium chloride, trioctylmethylammonium chloride, dodecyltrimethylammonium chloride, and tetradecyltrimethylammonium chloride.

Further, the catalyst is selected from one or more of the group consisting of polyethylene glycol dimethyl ether, 18-crown-6, and tetrabutylammonium bromide.

Further, based on the weight of 3-ethyl-3-hydroxymethyloxetane, the catalyst is added in an amount of 0.1% to 5% by weight.

Further, based on the weight of 3-ethyl-3-hydroxymethyloxetane, the catalyst is added in an amount of 0.5% to 2% by weight.

Further, the reaction temperature of the etherification reaction is 10 to 60° C., and the residence time of materials is 2 to 5 min.

Further, the device used in the separation step includes: a secondary thin-film evaporation device or a rectification tower.

Further, the microreactor has a reaction channel having an inner diameter of 500 to 8,000 μm.

By applying the technical solution of the invention, the microreactor has the advantages such as high heat and mass transfer coefficient, good mixing performance, easy temperature control, and safe and controllable process as compared to conventional reactors. The advantages by use of a microreactor in the preparation of oxetane derivative can greatly improve the mass and heat transfer performances of the reaction system, reduce the reaction time, improve the production efficiency, improve the product yield, realize the process continuity and automation, and improve the process safety. Limiting the aperture of the reaction channel of the microreactor within the above-mentioned range is beneficial to improving the selectivity of the etherification reaction, thereby contributing to improving the conversion rate of the oxetane derivative. In addition, the above synthesis process requires small size for reaction device, small floor space for production site, and less manpower, and has high safety.

DESCRIPTION OF THE DRAWINGS

The accompanying drawing as a part of the subject application is used to provide further understandings on the invention. The exemplary embodiments and their descriptions in the invention are used to explain the invention and do not serve as improper limitations to the invention. In the accompanying drawing:

FIG. 1 shows a schematic diagram for the structure of a device for preparing an oxetane derivative provided according to a typical embodiment of invention.

Among others, the above drawing includes the following reference signs:

10. Micromixer; 11. Organic raw material storage tank; 12. Base solution storage tank; 20. Microreactor; 21. Buffer tank; 30. Phase separation tank; 31. Waste water storage tank; 32. Organic phase storage tank; 40. Primary thin-film evaporator; 41. Crude product storage tank; 42. Recovered raw material storage tank; 50. Secondary thin-film evaporator; 51. Finished product storage tank; 52. Reboiler storage tank;

101. Organic raw material feeding pump; 102. Raw material feeding pump; 103. Feeding pump for primary thin-film evaporator; 104. Feeding pump for secondary thin-film evaporator.

DESCRIPTION OF EMBODIMENTS

It should be noted that, in the case of no conflict, the embodiments in the subject application as well as the features therein can be combined with each other. The invention will be described in detail below with reference to the embodiments.

As described in the background, the existing synthesis methods for oxetane derivatives have problems such as long reaction time, cumbersome operations, and poor safety. In order to solve the above technical problems, the invention provides a synthesis method for synthesizing an oxetane derivative by a microreactor, the oxetane derivative having the structure shown in Formula (I):

Formula (I)

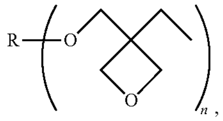

wherein R is a $C_2$ to $C_{12}$ linear or branched alkyl, an alkyl containing ethylene oxide structure, an alkyl containing oxetane structure, phenyl, tolyl, benzyl, or biphenyl, and n is 1-4; this method for synthesizing an oxetane derivative including: feeding 3-ethyl-3-hydroxymethyloxetane, a raw material Ha, a catalyst, and a base into a microreactor for etherification reaction to obtain an etherification product system, wherein the raw material Ha has a general formula of $R-(X)_n$, and X is halogen; and subjecting the etherification product system to separation to obtain the oxetane derivative.

The microreactor has the advantages such as high heat and mass transfer coefficient, good mixing performance, easy temperature control, and safe and controllable process as compared to conventional reactors. The advantages by use of a microreactor in the preparation of oxetane derivative can greatly improve the mass and heat transfer performances of the reaction system, reduce the reaction time, improve the production efficiency, improve the product yield, realize the process continuity and automation, and improve the process safety. In addition, the above synthesis process requires small size for reaction device, small floor space for production site, and less manpower, and has high safety.

Preferably, the microreactor has a reaction channel having an inner diameter of 200 to 10,000 μm. Limiting the aperture of the reaction channel of the microreactor within the above-mentioned range is beneficial to improving the selectivity of the etherification reaction, and further improves the conversion rate of the oxetane derivative. For example, the microreactor has a reaction channel having an inner diameter of 200 μm, 500 μm, 4,000 μm, 6,000 μm, 8,000 μm, or 10,000 μm, and more preferably, the microreactor has a reaction channel having an inner diameter of 500 to 8,000 μm.

In the above synthesis method, the base is an alkali metal compound or an aqueous solution of alkali metal compound. The alkali metal compound can be selected from those commonly used in the art. Preferably, the alkali metal compound includes but is not limited to one or more of the group consisting of lithium hydroxide, sodium hydroxide, potassium hydroxide, and calcium hydroxide; more preferably, the alkali metal compound is sodium hydroxide; and the concentration of the aqueous solution of alkali metal compound is 10% to 20%.

In the above synthesis method, the catalyst can be selected from those commonly used in the art. The catalyst includes but is not limited to one or more of the group consisting of polyethers, cyclic polyethers, and quaternary ammonium salts. Preferably, the catalyst includes but is not limited to one or more of the group consisting of polyethylene glycol, polyethylene glycol alkyl ether, 18-crown-6, 15-crown-5, tetraethylammonium bromide, tetrabutylammonium bromide, tetrabutylammonium chloride, trioctylmethylammonium chloride, dodecyltrimethylammonium chloride, and tetradecyltrimethylammonium chloride. Compared with other catalysts, the use of the above catalysts is beneficial to further improving the reaction rate of etherification reaction and shortening the reaction period. More preferably, the catalyst includes but is not limited to one or more of the group consisting of polyethylene glycol dimethyl ether, 18-crown-6, and tetrabutylammonium bromide.

In a preferred embodiment, based on the weight of 3-ethyl-3-hydroxymethyloxetane, the catalyst is added in an amount of 0.1% to 5% by weight. The amount of the catalyst includes but is not limited to the above-mentioned range, while limiting it within the above-mentioned range is beneficial to further improving the reaction rate of the etherification reaction. For example, based on the weight of 3-ethyl-3-hydroxymethyloxetane, the catalyst is added in an amount of 0.1%, 0.5%, 1%, 1.5%, 2%, 3%, or 4% by weight. More preferably, based on the weight of 3-ethyl-3-hydroxymethyloxetane, the catalyst is added in an amount of 0.5% to 2% by weight.

In a preferred embodiment, the molar ratio of 3-ethyl-3-hydroxymethyloxetane to the halogen in the raw material Ha is 1:(1.0 to 1.2). The molar ratio of 3-ethyl-3-hydroxymethyloxetane to the halogen in the raw material Ha includes but is not limited to the above-mentioned range, while limiting it within the above-mentioned range is beneficial to improving the conversion rate of 3-ethyl-3-hydroxymethyloxetane.

In a preferred embodiment, the reaction temperature of the etherification reaction is 10 to 60° C., and the residence time of materials is 2 to 5 min. The reaction temperature of the etherification reaction and the residence time of materials include but are not limited to the above-mentioned ranges, while limiting them within the above-mentioned ranges is beneficial to further improving the yield of the etherification product. For example, the reaction temperature of the etherification reaction can be 10° C., 20° C., 30° C., 40° C., 50° C., or 60° C.

The above separation step can be conducted using a device commonly used in the art. Preferably, the device used in the separation step includes: a secondary thin-film evaporation device or a rectification tower.

The subject application is further described in detail below with reference to specific examples, which cannot be understood as limiting the claimed scope in the subject application.

In the examples, the device shown in FIG. 1 was used to prepare the oxetane derivative, and the synthesis method included the following steps:

(1) The stoichiometric amounts of 3-ethyl-3-hydroxymethyloxetane (MOX101) and raw material R-$(X)_n$ were mixed well and charged into the organic raw material storage tank 11, and the base solution and the catalyst were mixed well and charged into the base solution storage tank 12.

(2) The microreactor 20, the primary thin-film evaporator 40, and the secondary thin-film evaporator 50 were adjusted to the set temperatures; the organic raw material feeding pump 101 and raw material feeding pump 102 were turned on, such that the raw materials entered into the micromixer 10 and mixed, remained in the microreactor 20 for a period, then entered into the buffer tank 21; and the organic phase was taken for detecting the conversion rate by GC.

(3) After a certain amount of materials were accumulated in the buffer tank 21, the materials entered into the phase separation tank 30, the organic phase and the aqueous phase were separated by standing, and the two phases entered into the waste water storage tank 31 and the organic phase storage tank 32 respectively.

(4) The feeding pump 103 for primary thin-film evaporator was turned on, and the organic phase was separated through the primary thin-film evaporator 40 to recover excess raw materials and obtain the crude product, wherein the recovered raw materials were stored in the recovered raw material storage tank 42, and the crude product was stored in the crude product storage tank 41; the feeding pump 104 for secondary thin-film evaporator was turned out, and the crude product entered into the secondary thin-film evaporator 50 for purification to obtain the product, wherein the finished product was stored in the finished product storage tank 51, and the reboiler was stored in the reboiler storage tank 52. The process parameters in Examples 1 to 9 were shown in Table 1 and Table 2.

TABLE 1

| Parameter | Example 1 | Example 2 | Example 3 | Example 4 | Example 5 |
|---|---|---|---|---|---|
| Microchannel device system | Shanghai Timo Fluid Technology Co., Ltd., TML/U/LL01, with an inner diameter of the microreactor channel of 4,000 μm | | | | |
| Weight of MOX101, g | 232.0 | 232.0 | 232.0 | 232.0 | 232.0 |
| Type of R-(X)n | a | b | c | d | e |
| Weight of R-(X)n, g | 222.0 | 322.8 | 303.6 | 152.4 | 210.0 |
| Type of base solution | 20% sodium hydroxide | 20% sodium hydroxide | 20% sodium hydroxide | 20% sodium hydroxide | 20% sodium hydroxide |
| Weight of base solution, g | 440.0 | 440.0 | 440.0 | 440.0 | 440.0 |
| n(MOX101):n (X):n (base) | 1:1.2:1.1 | 1:1.2:1.1 | 1:1.2:1.1 | 1:1.2:1.1 | 1:1.2:1.1 |
| Type of catalyst | Polyethylene glycol dimethyl ether | 18-Crown-6 | Tetrabutyl-ammonium bromide | 18-Crown-6 | Tetrabutyl-ammonium bromide |
| Amount of catalyst added | 1.160 g (0.5%) | 2.784 g (1.2%) | 4.640 g (2.0%) | 2.320 g (1.0%) | 2.320 g (1.0%) |
| Flow rate for raw material feeding pump, mL/min | 17.3 | 20.8 | 20.1 | 16.8 | 17.1 |
| Flow rate for base solution feeding pump, mL/min | 15.0 | 15.0 | 15.0 | 15.0 | 15.0 |
| Reaction temperature, ° C. | 40 | 50 | 60 | 60 | 60 |
| Residence time, min | 2 | 2 | 2 | 3 | 3 |
| Conversion rate for MOX101, % | 96.6 | 94.3 | 95.1 | 95.6 | 92.8 |
| Type of target product | A | B | C | D | E |
| Selectivity for target product, % | 95.8 | 96.7 | 96.4 | 96.0 | 97.2 |
| Heating temperature and pressure for primary thin-film evaporator | 100° C., 50 mmHg | 100° C., 10 mmHg | 120° C., 10 mmHg | 120° C., 10 mmHg | 120° C., 5 mmHg |
| Heating temperature and pressure for secondary thin-film evaporator | 100° C., 5 mmHg | 120° C., 5 5 mmHg | 130° C., 5 mmHg | 130° C., 5 mmHg | 130° C., 1 mmHg |

TABLE 1-continued

| Parameter | Example 1 | Example 2 | Example 3 | Example 4 | Example 5 |
|---|---|---|---|---|---|
| Weight of finished product, g | 285.9 | 344.5 | 339.5 | 234.2 | 265.2 |
| Yield for finished product, wt % | 83.1 | 80.5 | 82.4 | 81.9 | 79.4 |

Appendix: R-(X)n types and corresponding product types a 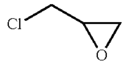

Epichlorohydrin b 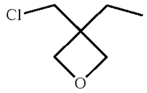

3-Ethyl-3chloromethyloxetane c 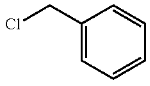

Benzyl chloride d 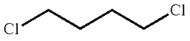

1,4-Dichlorobutane e 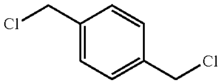

1,4-Dichloro-p-xylene

A 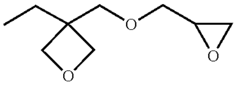

3-Ethyl-3-[(oxiranyl-2-methoxy)methyl]oxetane

B 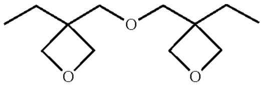

Bis[1-ethyl(3-oxetanyl)methyl]ether

C 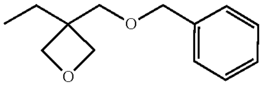

3-Benzyloxymethyl-3-ethyloxetane

D 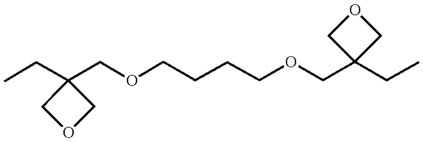

3-ethyl-3-[4-[(3-ethyloxetan-3-yl)methoxy[butoxymethyl]oxetane

E 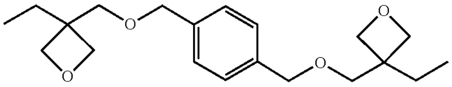

1,4-Bis[3-ethyl-3-oxetanemethoxymethyl]benzene

TABLE 2

| Parameter | Example 6 | Example 7 | Example 8 | Example 9 |
|---|---|---|---|---|
| Microchannel device system | Shanghai Timo Fluid Technology Co., Ltd., TML/U/LL01, with an inner diameter of the microreactor channel of 6,000 μm | | | |
| Weight of MOX101, g | 232.0 | 232.0 | 232.0 | 232.0 |
| Type of R-(X)n | f | g | h | i |
| Weight of R-(X)n, g | 356.4 | 356.4 | 151.6 | 126.0 |
| Type of base solution | 20% sodium hydroxide | 20% sodium hydroxide | 20% sodium hydroxide | 20% sodium hydroxide |

TABLE 2-continued

| Parameter | Example 6 | Example 7 | Example 8 | Example 9 |
|---|---|---|---|---|
| Weight of base solution, g | 440.0 | 440.0 | 440.0 | 440.0 |
| n(MOX101):n (X):n (base) | 1:1.2:1.1 | 1:1.2:1.1 | 1:1.2:1.1 | 1:1.2:1.1 |
| Type of catalyst | Tetrabutylammonium bromide | 18-Crown-6 | Tetrabutyl-ammonium bromide | 18-Crown-6 |
| Amount of catalyst added | 1.160 g (0.5%) | 2.784 g (1.2%) | 4.640 g (2.0%) | 2.320 g (1.0%) |
| Flow rate for raw material feeding pump, mL/min | 22.0 | 22.0 | 14.5 | 13.5 |
| Flow rate for base solution feeding pump, mL/min | 15.0 | 15.0 | 15.0 | 15.0 |
| Reaction temperature, ° C. | 10 | 20 | 30 | 40 |
| Residence time, min | 2 | 2 | 2 | 3 |
| Conversion rate for MOX101, % | 92.7 | 93.0 | 94.1 | 95.4 |
| Type of target product | F | G | H | I |
| Selectivity for target product, % | 97.3 | 96.8 | 96.5 | 95.2 |
| Heating temperature and pressure for primary thin-film evaporator | 100° C., 10 mmHg | 100° C., 10 mmHg | 100° C., 10 mmHg | 130° C., 10 mmHg |
| Heating temperature and pressure for secondary thin-film evaporator | 120° C., 5 mmHg | 120° C., 5 mmHg | 120° C., 1 mmHg | 140° C., 1 mmHg |
| Weight of finished product, g | 372.6 | 378.1 | 238.0 | 213.6 |
| Yield for finished product, wt % | 81.5 | 82.7 | 83.3 | 81.1 |

Appendix: R-(X)n types and corresponding product types f

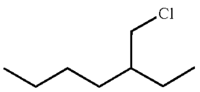

Chloro-iso-octane g

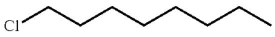

1-Chloro-octane h

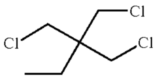

1,1,1-Tri(chloromethyl)propane i

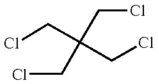

Tetrachloroneopentane

F

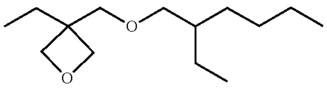

3-Ethyl-3-[[(2-ethylhexyl)oxy]methyl]oxetane

G

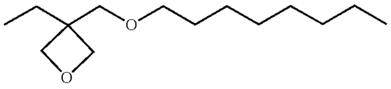

3-Ethyl-3-((octoxy)methyl)oxetane

H

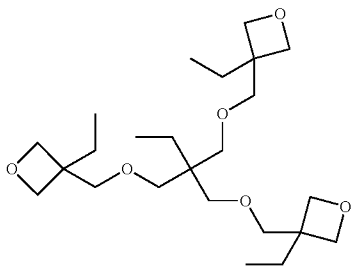

3-[2,2-Bis[(3-ethyloxa-3-yl)methoxymethyl]butoxymethyl]-3-ethyloxetane

TABLE 2-continued

| Parameter | Example 6 | Example 7 | Example 8 | Example 9 |
|---|---|---|---|---|
| I 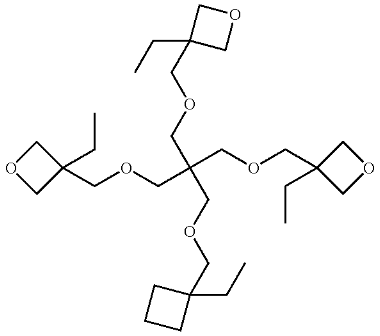 3,3′-(((2-((((1-Ethylcyclobutyl)methoxy)methyl)-2-((((3-ethyloxetan-3-yl)methoxy)methyl)propan-1,3-diyl)bis(oxy))bis(methylene))bis(3-ethyloxetane) | | | | |

Example 10

It differed from Example 1 in that: the microreactor has a reaction channel having an inner diameter of 200 μm.

The selectivity for 3-ethyl-3-[(oxiranyl-2-methoxy)methyl]oxetane was 90.5%, with a yield of 74.6%.

Example 11

It differed from Example 1 in that: the microreactor has a reaction channel having a size of 10,000 μm.

The selectivity for 3-ethyl-3-[(oxiranyl-2-methoxy)methyl]oxetane was 95.2%, with a yield of 76.7 wt %.

Example 12

It differed from Example 1 in that: the catalyst was added in an amount of 1.0%, the catalyst was polyethylene glycol dimethyl ether, and the residence time of materials was 5 min.

The selectivity for 3-ethyl-3-[(oxiranyl-2-methoxy)methyl]oxetane was 94.4%, with a yield of 82.4 wt %.

Example 13

It differed from Example 1 in that: the catalyst was added in an amount of 1.0%, the catalyst was 18-crown-6, and the residence time of materials was 4 min.

The selectivity for 3-ethyl-3-[(oxiranyl-2-methoxy)methyl]oxetane was 95.2%, with a yield of 81.9 wt %.

Example 14

It differed from Example 1 in that: the catalyst was added in an amount of 1.0%, the catalyst was polyethylene glycol, and the residence time of materials was 4 min.

The selectivity for 3-ethyl-3-[(oxiranyl-2-methoxy)methyl]oxetane was 96.2%, with a yield of 80.5 wt %.

Example 15

It differed from Example 1 in that: the catalyst was added in an amount of 1.0%, the catalyst was tetradecyltrimethylammonium chloride, and the residence time of materials was 5 min.

The selectivity for 3-ethyl-3-[(oxiranyl-2-methoxy)methyl]oxetane was 95.4%, with a yield of 82.4 wt %.

Example 16

It differed from Example 1 in that: the reaction temperature of the etherification reaction was 30° C.

The selectivity for 3-ethyl-3-[(oxiranyl-2-methoxy)methyl]oxetane was 92.8%, with a yield of 72.4 wt %.

Example 17

It differed from Example 1 in that: the microreactor has a reaction channel having a size of 12,000 μm.

The selectivity for 3-ethyl-3-[(oxiranyl-2-methoxy)methyl]oxetane was 90.8%, with a yield of 67.5 wt %.

Example 18

It differed from Example 1 in that: the stoichiometric amounts of 3-ethyl-3-hydroxymethyloxetane (MOX101), caustic soda flakes, and catalyst were mixed well and charged into the organic raw material storage tank 11, and epichlorohydrin was charged into the raw material storage tank 12, wherein the microreactor has a reaction channel having an inner diameter of 500 μm.

The selectivity for 3-ethyl-3-[(oxiranyl-2-methoxy)methyl]oxetane was 95.0%, with a yield of 80.6%.

Example 19

It differed from Example 1 in that: the stoichiometric amounts of 3-ethyl-3-hydroxymethyloxetane (MOX101), epichlorohydrin, and catalyst were mixed well and charged into the organic raw material storage tank 11, and the base solution was charged into the raw material storage tank 12, wherein the microreactor has a reaction channel having an inner diameter of 8,000 μm.

The selectivity for 3-ethyl-3-[(oxiranyl-2-methoxy)methyl]oxetane was 95.6%, with a yield of 82.3 wt %.

Example 20

It differed from Example 1 in that: the reaction temperature of the etherification reaction was 100° C.

The selectivity for 3-ethyl-3-[(oxiranyl-2-methoxy) methyl]oxetane was 94.6%, with a yield of 76.1 wt %.

Example 21

It differed from Example 1 in that: the reaction temperature of the etherification reaction was 5° C.

The selectivity for 3-ethyl-3-[(oxiranyl-2-methoxy) methyl]oxetane was 85.9%, with a yield of 72.4 wt %.

Example 22

It differed from Example 1 in that: the catalyst was added in an amount of 0.1%, the catalyst was tetrabutylammonium bromide, and the residence time of materials was 5 min.

The selectivity for 3-ethyl-3-[(oxiranyl-2-methoxy) methyl]oxetane was 90.3%, with a yield of 73.5 wt %.

Example 23

It differed from Example 1 in that: the stoichiometric amounts of 3-ethyl-3-hydroxymethyloxetane (MOX101) and caustic soda flakes were mixed well and charged into the organic raw material storage tank 11, and epichlorohydrin and catalyst were charged into the raw material storage tank 12, wherein the catalyst was added in an amount of 5%, the catalyst was 18-crown-6, and the residence time of materials was 2 min.

The selectivity for 3-ethyl-3-[(oxiranyl-2-methoxy) methyl]oxetane was 92.1%, with a yield of 78.3 wt %.

Example 24

It differed from Example 1 in that: the stoichiometric amounts of 3-ethyl-3-hydroxymethyloxetane (MOX101) and caustic soda flakes were mixed well and charged into the organic raw material storage tank 11, and epichlorohydrin and catalyst were charged into the raw material storage tank 12, wherein the catalyst was added in an amount of 4%, the catalyst was tetrabutylammonium bromide, and the residence time of materials was 3 min.

The selectivity for 3-ethyl-3-[(oxiranyl-2-methoxy) methyl]oxetane was 91.7%, with a yield of 75.3 wt %.

In Comparative Examples 1 to 5, a conventional reactor was used to prepare the oxetane derivative, and the specific process parameters were shown in Table 3. The synthesis method included the following steps:

Into a four-necked flask 3-ethyl-3-hydroxymethyloxetane (MOX101) and raw material R-$(X)_n$ were added and stirred to mix well; the base solution and catalyst were mixed well and dropwise added into the above four-necked flask; after the dropwise addition was completed, the reaction was conducted under heat preservation; the organic phase was taken for detecting the conversion rate by GC, and the reaction was stopped after the conversion rate no longer changed;

and the reaction product system was allowed to stand for phase separation, then subjected to rectification to obtain the finished product.

TABLE 3

| Parameter | Comparative Example 1 | Comparative Example 2 | Comparative Example 3 | Comparative Example 4 | Comparative Example 5 |
|---|---|---|---|---|---|
| Weight of MOX101 (g) | 232.0 | 232.0 | 232.0 | 232.0 | 232.0 |
| Type of R-(X)n | a | b | c | d | e |
| Weight of R-(X)n | 222.0 g | 322.8 g | 303.6 g | 152.4 g | 210.0 g |
| Type of base solution | 20% sodium hydroxide | 20% sodium hydroxide | 20% sodium hydroxide | 20% sodium hydroxide | 20% sodium hydroxide |
| Weight of base solution | 440.0 g | 440.0 g | 440.0 g | 440.0 g | 440.0 g |
| n (MOX101):n (X):n(base) | 1:1.2:1.1 | 1:1.2:1.1 | 1:1.2:1.1 | 1:1.2:1.1 | 1:1.2:1.1 |
| Type of catalyst | Polyethylene glycol dimethyl ether | 18-Crown-6 | Tetrabutylammonium bromide | 18-Crown-6 | Tetrabutylammonium bromide |
| Amount of catalyst added | 1.160 g (0.5%) | 2.784 g (1.2%) | 4.640 g (2.0%) | 2.320 g (1.0%) | 2.320 g (1.0%) |
| Reaction temperature | 40° C. | 50° C. | 60° C. | 60° C. | 60° C. |
| Reaction time | 4 h | 4 h | 5 h | 4.5 h | 5 h |
| Conversion rate for MOX101 | 84.5% | 81.6% | 83.3% | 80.7% | 78.8% |
| Type of target product | A | B | C | D | E |
| Selectivity for target product | 80.2% | 81.5% | 78.2% | 74.1% | 73.2% |
| Weight of finished product | 197.5 g | 235.4 g | 219.2 g | 147.0 g | 167.7 g |
| Yield for finished product | 57.4% | 55.0% | 53.2% | 51.4% | 50.2% |

From the above descriptions, it can be seen that the above embodiments of the invention achieve the following technical effects:

By comparing Examples 1 to 24 and Comparative Examples 1 to 5, it can be seen that adopting the method provided in the subject application is beneficial to the selectivity and yield of oxetane derivative.

By comparing Examples 1, 6, 10, 11, and 17 to 19, it can be seen that limiting the inner diameter of the reaction channel of the microreactor within the range of the subject application is beneficial to improving the selectivity and yield of oxetane derivative.

By comparing Examples 1, 16, 20, and 21, it can be seen that limiting the reaction temperature of the etherification reaction within the range of the subject application is beneficial to improving the selectivity and yield of oxetane derivative.

The above descriptions are merely preferred embodiments of the invention and are not intended to limit the invention. For those skilled in the art, the invention may have various modifications and changes. Any modification, equivalent replacement, and improvement made within the spirit and principle of the invention shall be included within the scope of the invention.

What is claimed is:

1. A synthesis method for synthesizing an oxetane derivative by a microreactor, the oxetane derivative having the structure shown in Formula (I):

Formula (I)

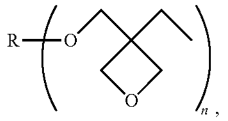

wherein R is a $C_2$ to $C_{12}$ linear or branched alkyl, an alkyl containing ethylene oxide structure, an alkyl containing oxetane structure, phenyl, tolyl, benzyl, or biphenyl, and n is 1-4;

the method comprising:

feeding 3-ethyl-3-hydroxymethyloxetane, a raw material Ha, a catalyst, and a base into a microreactor for etherification reaction to obtain an etherification product system, wherein the raw material Ha has a general formula of $R-(X)_n$, and X is halogen; and subjecting the etherification product system to separation to obtain the oxetane derivative.

2. The method of claim 1, wherein the microreactor has a reaction channel having an inner diameter of 200 to 10,000 μm.

3. The method of claim 1, wherein the base is an alkali metal compound or an aqueous solution of alkali metal compound, and the alkali metal compound is selected from the group consisting of lithium hydroxide, sodium hydroxide, potassium hydroxide, and calcium hydroxide; and the concentration of the aqueous solution of alkali metal compound is 10% to 20%; and the catalyst is selected from the group consisting of polyethers, cyclic polyethers, and quaternary ammonium salts.

4. The method of claim 1, wherein the catalyst is selected from the group consisting of polyethylene glycol, polyethylene glycol alkyl ether, 18-crown-6, 15-crown-5, tetraethylammonium bromide, tetrabutylammonium bromide, tetrabutylammonium chloride, trioctylmethylammonium chloride, dodecyltrimethylammonium chloride, and tetradecyltrimethylammonium chloride.

5. The method of claim 4, wherein the catalyst is selected from the group consisting of polyethylene glycol dimethyl ether, 18-crown-6, and tetrabutylammonium bromide.

6. The method of claim 1, wherein, based on the weight of 3-ethyl-3-hydroxymethyloxetane, the catalyst is added in an amount of 0.1% to 5% by weight.

7. The method of claim 6, wherein, based on the weight of 3-ethyl-3-hydroxymethyloxetane, the catalyst is added in an amount of 0.5% to 2% by weight.

8. The method of claim 1, wherein the reaction temperature of the etherification reaction is 10 to 60° C., and the residence time of materials is 2 to 5 min.

9. The method of claim 8, wherein the separation step is performed in a secondary thin-film evaporation device or a rectification tower.

10. The method of claim 1, wherein the microreactor has a reaction channel having an inner diameter of 500 to 8,000 μm.

11. The method of claim 3, wherein the alkali metal compound is sodium hydroxide.

* * * * *